United States Patent [19]
Maynard

[11] Patent Number: 5,996,346
[45] Date of Patent: Dec. 7, 1999

[54] ELECTRICALLY ACTIVATED MULTI-JOINTED MANIPULATOR

[75] Inventor: Ronald S. Maynard, Sunnyvale, Calif.

[73] Assignee: The Board of Trustees of the Leland Stanford Junior University, Stanford, Calif.

[21] Appl. No.: 08/599,449

[22] Filed: Jan. 19, 1996

Related U.S. Application Data

[62] Division of application No. 08/099,369, Jul. 28, 1993, Pat. No. 5,556,370.

[51] Int. Cl.$^6$ .................................................... F03G 7/06
[52] U.S. Cl. .............................................. 60/527; 60/528
[58] Field of Search .............................. 600/151; 60/527, 60/528, 529

[56] References Cited

U.S. PATENT DOCUMENTS

| | | | |
|---|---|---|---|
| 4,790,624 | 12/1988 | Van Hoye et al. | 600/151 X |
| 5,035,530 | 7/1991 | Fukuda et al. | 60/527 X |
| 5,335,498 | 8/1994 | Komatsu et al. | 60/527 X |
| 5,556,370 | 9/1996 | Maynard | 600/151 |

*Primary Examiner*—Stephen Husar
*Attorney, Agent, or Firm*—Morrison & Foerster, LLP

[57] ABSTRACT

A joint assembly having a plurality of concatenated joints, each actuated by a negative coefficient of expansion material such Ti Ni, is capable of performing highly dexterous maneuvers in three dimensions without built in torsional stiffness. The Ti Ni actuators are coiled around the body of opposing joint halves and are capable of maximizing large angular motion while making the joint dimensions as compact as possible. The actuators also operate with low current and thereby minimize heat dissipation.

27 Claims, 13 Drawing Sheets

Figure 1 - Generalized Joint Description

ELECTRICALLY ACTIVATED MULTI-JOINTED MANIPULATOR

This application is a divisional of application Ser. No. 08/099,369, filed Jul. 28, 1993, now U.S. Pat. No. 5,556,370.

BACKGROUND

The field of the present invention relates generally to electrically articulated devices using shape memory alloy (SMA) actuators. In particular, the field of the present invention relates to an improved electrically articulated multi-jointed manipulator which is adapted to be used as an endoscope, bronchoscope or a multi-jointed probe for robotic applications.

Conventional endoscopes are currently so-called "pull wire" devices which are used in conjunction with highly invasive surgery techniques. Typically, a conventional endoscope is insertable into a body cavity of a patient such as the colon, or bronchial tree (in the case of a bronchoscope) for performing a surgical operation. Conventional endoscopes or the like are simply pushed into a body cavity until they encounter an obstruction. Since conventional endoscopes and bronchoscopes are incapable of independent rotation when inserted into a body cavity, they presently cannot be maneuvered around an obstruction. Consequently, conventional endoscopes, bronchoscopes or like surgical implements pose serious risk of injury to delicate tissue. The invasive trauma to a patient caused by the use of a conventional endoscope, bronchoscope or the like is severe.

Attempts to use shape memory alloy (SMA) actuators to steer a conventional endoscope, bronchoscope, or the like until now have failed due to the large dimensions of the typical endoscope and the need for large current carrying feed wires to actuate such a large device. The large current carrying wires make a conventional SMA actuated device extremely bulky. The large wires thereby limit the total number of actuators and substantially reduce the maneuverability of an endoscope. Due to the need for large current carrying wires, conventional SMA endoscopes have not been built with more than two joints and are limited to two axes of actuation. Therefore, the conventional SMA actuated endoscopes presently have approximately the same capability of a pull wire endoscope. However, conventional SMA actuated endoscopes can cause an increase in invasive trauma which exceeds that of more pliable pull wire endoscopes which are simply pushed into place.

The large current carrying wires necessary to drive conventional SMA actuated endoscopes, bronchoscope, or the like also cause increased heat build up within the endoscope device. This has the disadvantage that heat must be dissipated through the body of the patient, causing the risk of burns. Accordingly, the invasive trauma caused by a conventional SMA actuated endoscope, bronchoscope, or the like is considerable and poses a serious risk of injury.

A further disadvantage of conventional pull wire endoscopes is that they are severely limited in their range of movement. The tip of such an endoscope is capable of being deflected in only a single plane.

Another problem with attempts to steer endoscopes by conventional SMA actuators is that a negative coefficient of expansion material such as a 50:50 or 49:51 formulation of titanium nickel (TiNi) is limited to a usable strain of only approximately 5% of its total length. Thus, it is impossible to obtain large or useful angular motion from a conventional SMA actuated joint.

Conventional SMA steerable devices operate by using a joint comprising two halves which are moved in different directions by antagonistically configured strips or actuator bands of 49:51 TiNi. Upon being resistively heated by application of an electric current, one of the TiNi bands contracts and imparts movement to one half of the joint. However, because conventional SMA actuators configured as negative coefficient of expansion materials are limited to a usable strain of only 5% of total length, they must be made extremely long in order to derive useful movement. This has the disadvantage of increasing the size of the joint, thereby increasing bulk and the risk of invasive trauma.

Since SMA actuators are current driven devices, the large size of a conventional SMA actuator also necessitates a large diameter wire for providing the activation current for resistively heating the joint to its activation threshold. This also creates undesirable bulk and problems of heat dissipation as set forth above.

Conventional means for actively steering a device such as an endoscope for performing dexterous surgical maneuvers suffer from a further disadvantage of torsional rigidity. Presently, the body of an endoscope must be rotated by hand about the longitudinal axis to cause the tip of the endoscope to reach a different point within the patient. Conventional endoscopes therefore must be maintained torsionally rigid over their entire length. When a torsionally rigid endoscope is rotated in order to move the tip in a desired direction, extreme trauma to tissue can result since the entire torsionally rigid body of the endoscope also must be rotated.

The torsionally stiff body of a conventional endoscope, when positioned in a convoluted path, places large incidental forces on the walls of a vessel through the action of making a rotation. There are two contributions to the incidental forces. The first results from moving a convoluted shape in a rotation. The other contribution to the incidental force results from the inherent stiffness of a conventional endoscope. What is needed is an endoscope or multi-jointed probe which has the advantage of being extremely maneuverable and pliable, but at the same time can be rotated and execute highly dexterous maneuvers in three dimensions.

What is needed is a new type of endoscope which can perform highly dexterous maneuvers in three dimensions without built in torsional stiffness. Such an endoscope would be steerable without torsional rigidity to perform complex maneuvers and would be minimally invasive.

What is also needed is an improved method and apparatus for actively steering a surgical device such as an endoscope, bronchoscope or the like with a minimum of invasive trauma to a patient and which would provide tactile feedback to the operating physician without torsional rigidity.

It would also be highly desirable to provide an improved SMA actuator joint with a greater range of motion, while at the same time minimizing the size of such a joint. Such an improved SMA actuator joint would operate on low current to minimize heat dissipation and also would be more maneuverable due to its smaller size. What is also needed is an improved low current SMA actuator joint which would capable of imparting sufficient torque to an endoscope, bronchoscope or the like to provide extreme dexterity and maneuverability over a wide range of motion. The elimination of bulky current carrying feed wires would provide a significant advance in minimally invasive surgical procedures over conventional endoscopes.

What is also needed is an improved control system for providing visual feedback for accurately positioning and steering an endoscope or similar surgical device within a patient. Such a control system would advantageously be capable of performing highly dexterous maneuvers in three dimensions.

SUMMARY

In order to overcome the above discussed disadvantages of conventional pull wire endoscopes and steerable endoscopes using shape memory alloy actuators, one aspect of the present invention comprises an electrically articulated joint for an endoscope, multi-jointed manipulator, or the like comprising a pair of electrically actuated elements and a simple mechanical linkage that permits a wide range of angular movement in a single plane. The joint comprises a first half and a second half movably connected at a joint axis with the first half providing one or more degrees of freedom with respect to the first half. The joint is essentially hollow and will transmit torque in a direction perpendicular to its axis of articulation.

In practice, ten to twenty joints are assembled with each axis of articulation perpendicular to a previous joint's axis. Electrical connections are made via a flexible, multiconductor cable. By placing the actuators and electrical cables on the joint's surface, a large channel is made available within the joint for fiber optic bundles and/or endoscopic surgical tools, or the like. With appropriate steering commands provided by a microprocessor, the assembly of joints can execute dexterous maneuvers in three dimensional space.

Joint articulation is achieved by heating one actuator element which in one aspect of the invention is comprised of a negative coefficient of thermal expansion material such as TiNi. Upon heating, the element contracts and produces a force which acts directly on the opposing joint half thereby producing joint rotation. The inactive opposing element is reversibly deformed as a result of this motion. The joint may be rotated in the opposite direction, or to any given position by providing current in the proper ratios to the two filaments. Natural conduction and convection carries waste heat from the actuating elements. The rate of heat dissipation governs the rate of operation.

Negative coefficient of expansion materials are limited to a usable strain of approximately 5% of total length. In order to obtain sufficiently large angular motions from a 5% contraction of the material, a an actuating element can be elongated or configured so as to be wrapped around the body of a joint to make the overall dimensions as compact as possible. In this arrangement, one end of the actuating coil is anchored to a pulley on the opposing joint half. The other end is fixed to the joint. The opposing joint has a similar coil arrangement. The coil elements are electrically insulated with teflon or a similar insulator which provides a low friction interface with the joint surface. One end of each coil is electrically grounded to the joint body while the other ends are independently driven by an external current source.

The actuating elements also take other forms. For example, the memory aspect of a shape memory alloy material such as TiNi can be utilized, wherein a memory metal spring is affixed to the outside of the joint. TiNi would comprise an excellent coil material due to its high strength, availability and wire form, and relatively large work output for a given volume. Resistively heating the TiNi spring would cause it to assume its memorized austenitic state and would provide an actuating torque. A TiNi spring of the same dimensions on the opposite side of the joint would produce motions in the opposite direction.

Other actuating materials also can be utilized to effect movement of the joint such as a thermal coefficient of expansion material which utilizes heat shrink tubing. This provides the advantage of a large coefficient of expansion with repeatable motion.

In accordance with another aspect of the invention, a plurality of joints are adapted to be concatenated. A microcable is provided for selectively activating the corresponding actuators for each joint. In this way the microcable provides a means for controllably or coordinating the activation of the plurality of concatenated joints. This enables the concatenated joint assembly to be controllably maneuvered to assume virtually any desired position in three dimensions for performing surgical functions or other applications requiring complex maneuvers in three dimensional space.

BRIEF DESCRIPTION OF THE DRAWINGS

These and other advantages of the present invention may be appreciated from studying the following detailed description of the invention together with the drawings in which.

DETAILED DESCRIPTION

Overview

Figure 1:
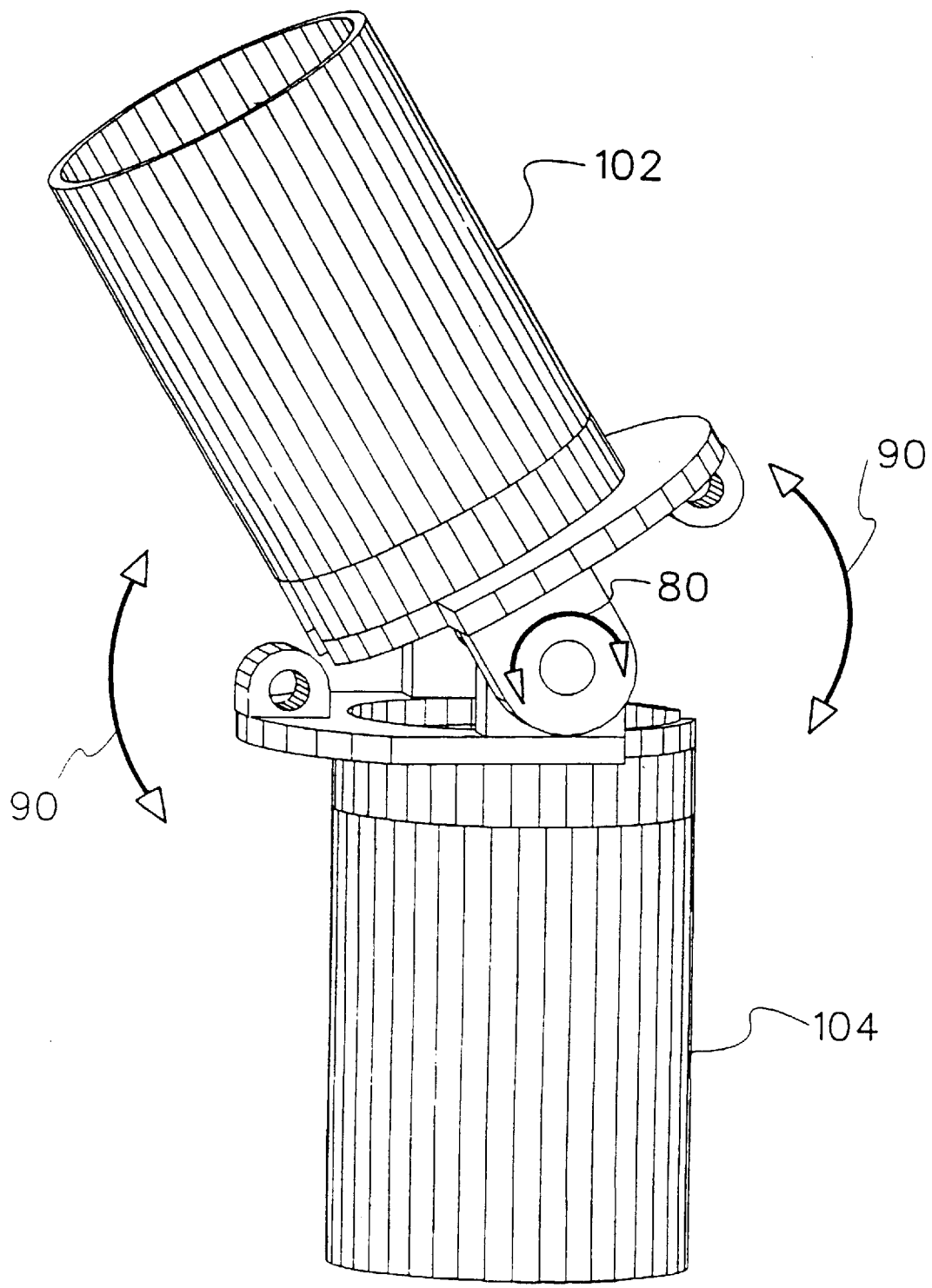
FIG. 1 shows a general joint configuration.

FIG. 1 shows a basic hollow mechanical joint assembly that permits relative angular motion between two joint halves in a single plane. A bending force is produced by applying torque 80 at the axis of rotation on one of the joint halves. A bending force also can be produced by applying a force couple 90 between the two joint halves.

Conventional SMA material such as wire has been used as the actuator element to provide a coupling force between the joint halves. However since SMA material typically contracts only 5% of its length, the useful bending forces which can be derived from the SMA effect are extremely limited.

In addition, conventional SMA activated joints must be unacceptably large to accommodate large current carrying feed wires to resistively heat the actuator element to its activation threshold. The feed wires in conventional devices typically carry a current of 3 amps. Thus, conventional SMA joint activated devices are typically limited to only two joints due to the size of the wires.

The large current carrying feed wires therefore impose severe size constraints on SMA activated endoscopes, bronchoscopes, or the like. The large feed wires also make a conventional SMA activated joint torsionally rigid and prone to cause injury to a patient when used for surgical intervention. The foregoing factors severely limit the maneuverability and usefulness of an endoscope or similar device which incorporates conventional SMA activated joints.

The aspects of the present invention provide improved actuator elements and materials for producing actuating forces. The present actuators are as compact as possible, are distributed about the periphery of the joint and generate large actuating forces and large excursions for increased maneuverability and extreme downsizing of the endoscopes, bronchoscopes, or the like, which incorporate SMA actuator joints. In accordance with another aspect of the invention, as explained infra, the actuator elements are designed to be resistively heated by only a minimum threshold activation current, thereby eliminating the large current carrying feed wires of conventional devices.

Figure 2:
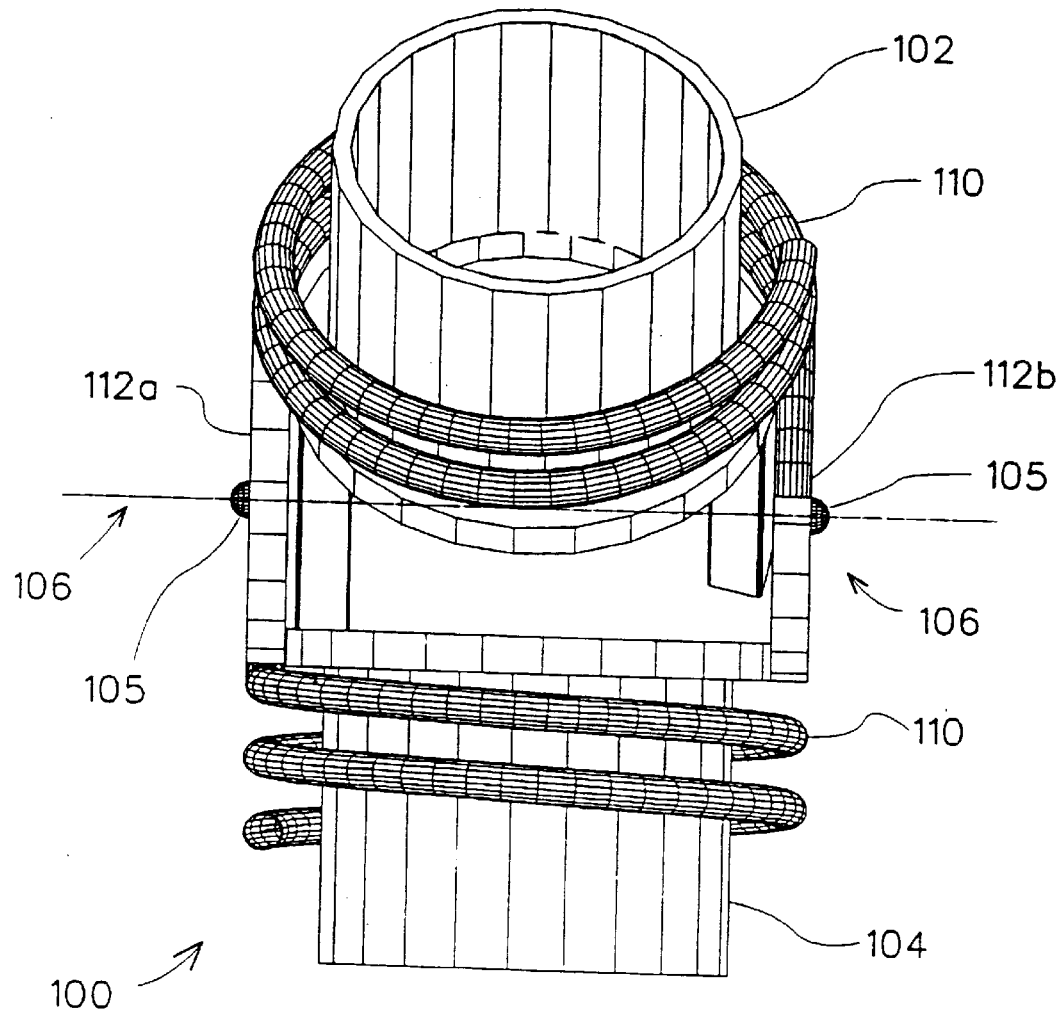
FIG. 2 shows a front view of a first embodiment according to the present invention.
Figure 3:
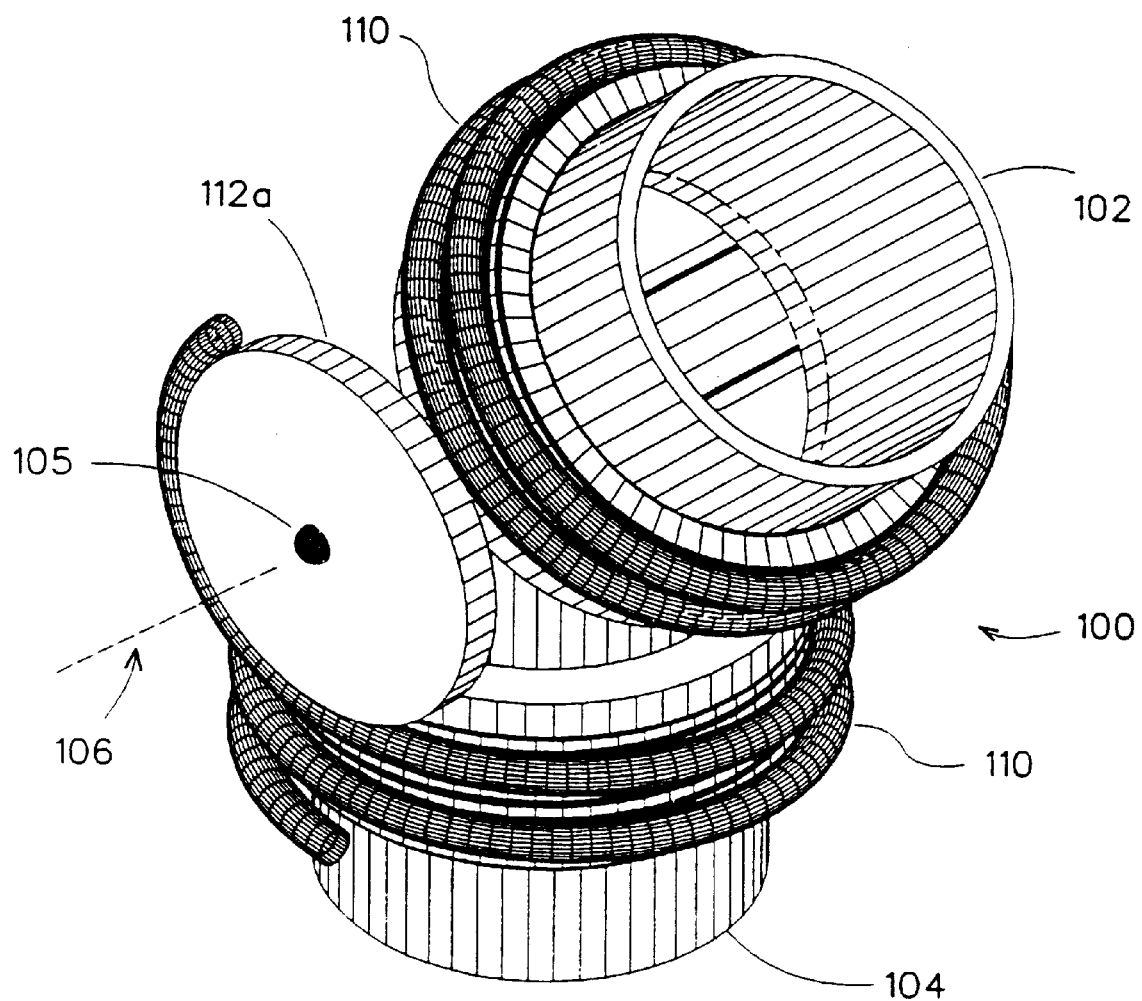
FIG. 3 shows a perspective view of embodiment of FIG. 2.

As shown in FIGS. 1–3, an electrically articulated joint 100 for an endoscope, bronchoscope, or multi-jointed manipulator comprises a first joint half 102 and second joint half 104. Both joint halves are connected together by a mechanical linkage 105 defining a joint axis 106 as shown.

Any convenient mechanical linkage is possible. For example, the mechanical linkage can be a simple bolt and fastener arrangement. What is important is that the mechanical linkage 105 provide a means for coupling the two joint halves 102 and 104 together at a joint axis 106. The second joint half 104 is movably connected at the joint axis 106 for providing one or more degrees of freedom with respect to the first joint half 102.

Note that if coupling 105 is elastic, two axes of rotation lying in the same plane could be provided. This advantageously would permit two degrees of freedom per joint. In this case, mechanical coupling 105 compresses a cylindrical membrane connecting the two halves. Thus, the electrically articulated joint assembly 100 for a multi-jointed manipulator consists of a simple mechanical linkage 105 that provides a large range of angular motion in a single plane. As can be seen from FIGS. 1 and 2, the joint assembly 100 is essentially hollow and will transmit torque in a direction perpendicular to the axis of articulation. An actuator means 110 is connected to the first and second joint halves 102 and 104, respectively, for providing a controllable bending force to the joint assembly 100 upon application of an electric current of a predetermined threshold value. The electric current is provided through conventional means which are well known to those skilled in the art and are omitted here for the sake of simplicity.

In one aspect of the invention as shown in FIGS. 2 and 3, actuator means 110 comprise one or more coils wrapped around the circumference of one of the joint halves 102, 104. The coils of actuator means 110 are disposed for providing bending forces upon application of an electric current sufficient to heat the actuator material to an activation threshold temperature. Actuator means 110 preferably comprises a material characterized by a negative co-efficient of expansion. Resistive heating of the actuator means 110 to an activation threshold is produced by passing an electrical current through the helical coils of the negative co-efficient of expansion material. The coils of the actuator means 110 comprise any material which possesses a negative co-efficient of thermal expansion, such as a formulation of 49:51 TiNi, 50:50 TiNi, or the like.

A titanium nickel (TiNi) formulation is an excellent coil material for actuator means 110 due to its high strength, availability in wire form, and relatively large work output per volume. However, conventional methods employing TiNi as an actuator means in a catheter or the like suffer from the disadvantage that TiNi is limited to only a 5% contraction.

In accordance with one aspect of the invention, in order to obtain sufficiently large angular motions from a 5% contraction of the coil of the actuator means 110, a long wire is used and is adapted to be wrapped around the circumference of the body of the first and second joint halves 102, 104 as shown in FIGS. 2 and 3. Wrapping the actuator means 110 around the body of the joint halves has the advantage of making the overall dimensions of the joint as small as possible, while at the same time maximizing the available amount of contraction of the actuator means 110.

It will be appreciated that a pair of pulleys, 112a, 112b are located on opposite sides of the joint assembly 100 and are disposed transversely to the axis of actuation 106. The pulleys 112a, 112b aid in obtaining a large angular motion from the 5% contraction of the coil of actuator means 110. The pulleys also enable the coil of actuator means 110 to be made as long as possible while minimizing the overall dimensions of the joint assembly 100. This has the advantage of maximizing the amount of contraction which can be obtained from the actuator means 110, while minimizing the dimensions of the joint.

One end of the coil of actuator means 110 is anchored to a pulley, for example 112a of the opposing joint half 102. The other end of the actuator means 110 is fixed with respect to the joint. The opposing joint half 104 has a similar coil arrangement.

In operation, one end of each coil of actuator means 110 is electrically grounded to the joint body 100 while the other ends are independently driven by an external current source in accordance with conventional techniques which are well-known to those skilled in the art. When the coil of actuator means 110 which is wrapped around joint half 104 is electrically heated to its activation threshold, it contracts and provides a force which attempts to rotate the pulley 112a of the opposing joint half 102. It will be appreciated that each pulley 112a, 112b is integrally connected with its corresponding joint half 102, 104, respectively, in order to transmit torque thereto.

In a typical operating condition, the opposite portion of the coil 110, associated with, for example, joint half 102, is not activated and is readily stretched to accommodate the rotary motion. Mechanical conversion of the rotation plane can be accomplished through other mechanical means such as a gear and pinion, fork and trunion combination and so forth. By disengaging one portion of actuator coil 200 and heating the opposite coil of actuator coil 200, the joint 100 can be made to rotate in the opposite direction.

Figure 4:
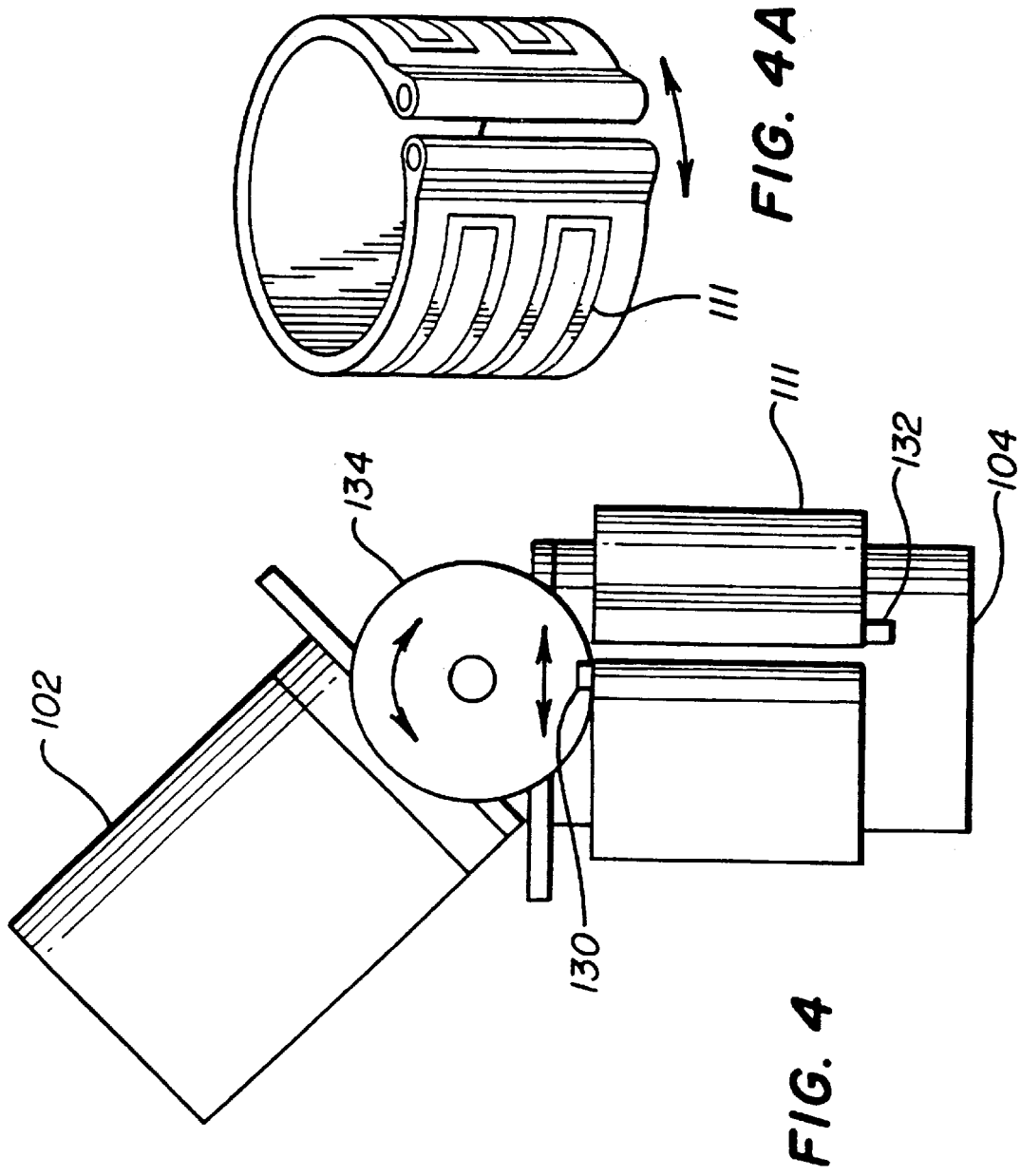
FIG. 4 shows a perspective view of another embodiment according to the present invention.

Referring to FIG. 4, an alternate embodiment of the present invention reduces the plurality of turns of actuator material 110 as shown in FIGS. 2 and 3 to a single turn. The single turn of actuator material 111 is disposed around the circumference of one joint half, 104 for example, such that motion along the longitudinal axis of the joint assembly formed by joint halves 102, 104 is transmitted along the axis of actuation.

The single turn of actuator means 111 also could be wrapped around the joint half 102 for providing a pulling force upon the application of an electric current when heated to an actuation temperature. Mechanical linkage means such as pulley and axle 134 are provided for joining each joint half 102, 104. The mechanical linkage also provides means for transforming the pulling force which occurs upon actuation of the actuator means 111 into a torque about the axis of actuation. Mechanical conversion of the rotation plane can be accomplished through the other mechanical means such as a gear and pinion, fork and trunion combination and so forth.

The actuator means 111 may be a solid shape memory alloy wire or a bundle of stranded SMA wires. What is important is that it be a material exhibiting a high coefficient of thermal expansion as previously explained with respect to FIG. 2. In this case, the actuator means 111 comprises an inner core of material exhibiting a high degree of negative coefficient of expansion. This core of actuator material is adapted to be sheathed by a teflon insulator and an outer sheath of conductive material such as nickel for ohmically heating the inner core of shape memory alloy actuator material, negative coefficient of expansion material or the like. This has the same advantages as previously described with respect to FIG. 2.

In the embodiment of FIG. 4, the single turn actuator means 111 may be configured as a folded continuous path of a material characterized by a large positive or negative coefficient of thermal expansion. Such a folded continuous path of actuation material is shown as exhibited in FIGS. 11–13. Any two adjacent segments of the folded path of material are electrically isolated with teflon or other insulator. In accordance with an aspect of the invention, the configuration of the actuator means 111 as a folded continuous path of a negative coefficient of expansion material such as TiNi, or the like permits the negative coefficient of expansion to be maximized for a given area. The maximizing of the length of the material for a given area not only maximizes the available amount of expansion but also maximizes the electrical resistance of the material 111. This has the advantage of reducing current demands when ohmically heating the shape memory actuator means 111 or other actuator material characterized by a large coefficient of thermal expansion.

A single turn actuator is advantageously employed in applications where it is desirable to reduce the frictional losses of a multi-turn actuator as previously described. In this aspect of the invention, each joint half 102, 104 is provided with a single turn actuator band 111. One edge of the single turn actuator 111 is fixed to the joint as shown at 132 in FIG. 4. Upon applying ohmic heating, the free end 130 of the actuator band contracts. The resulting circular motion is converted to motion along the bend axis of the joint through a mechanical means such as pulley 134 operatively connected with free end 130.

Figure 5:
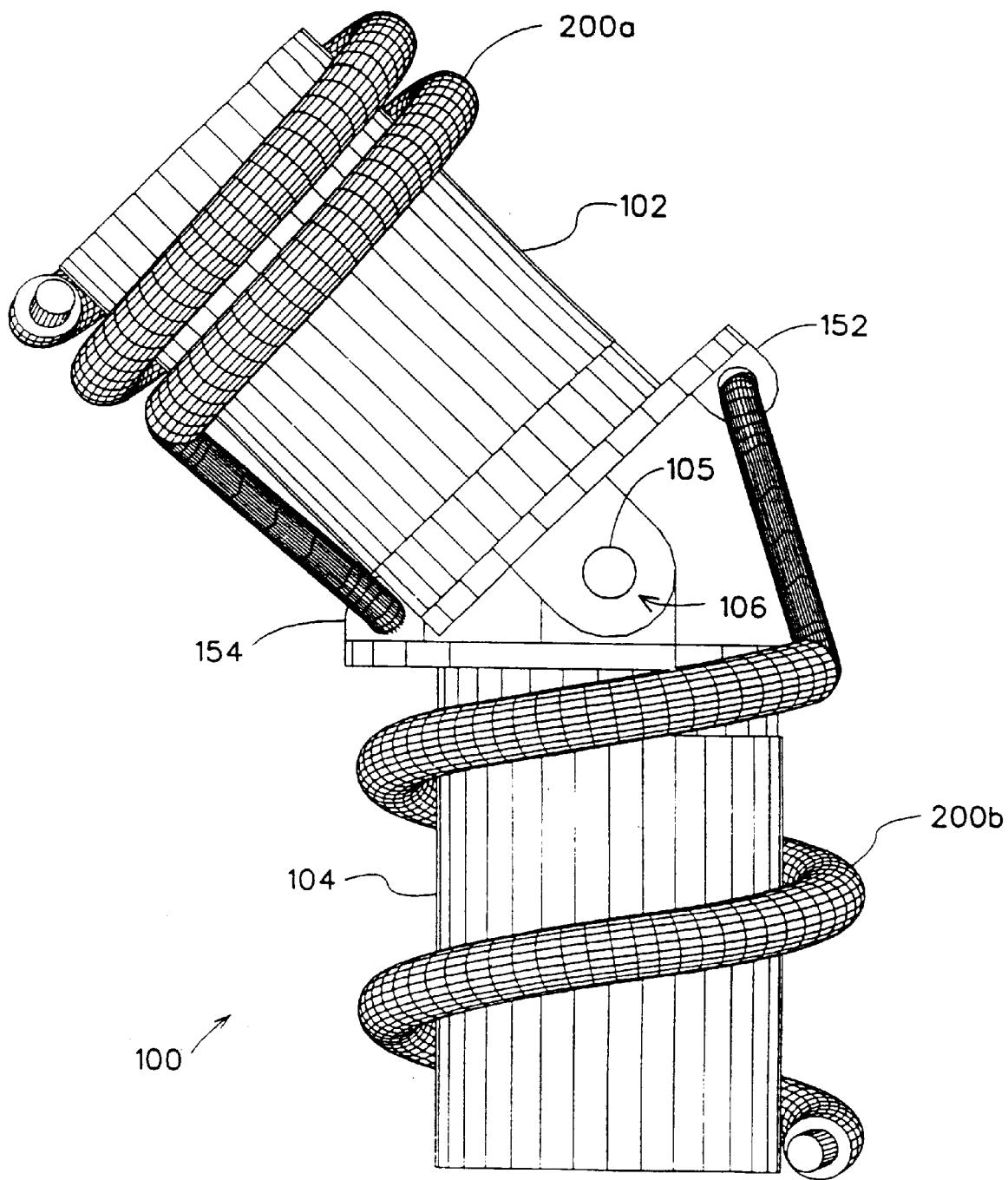
FIG. 5 shows a side view of a spring coil actuator according to an embodiment of the present invention as shown in FIG. 4.
Figure 6:
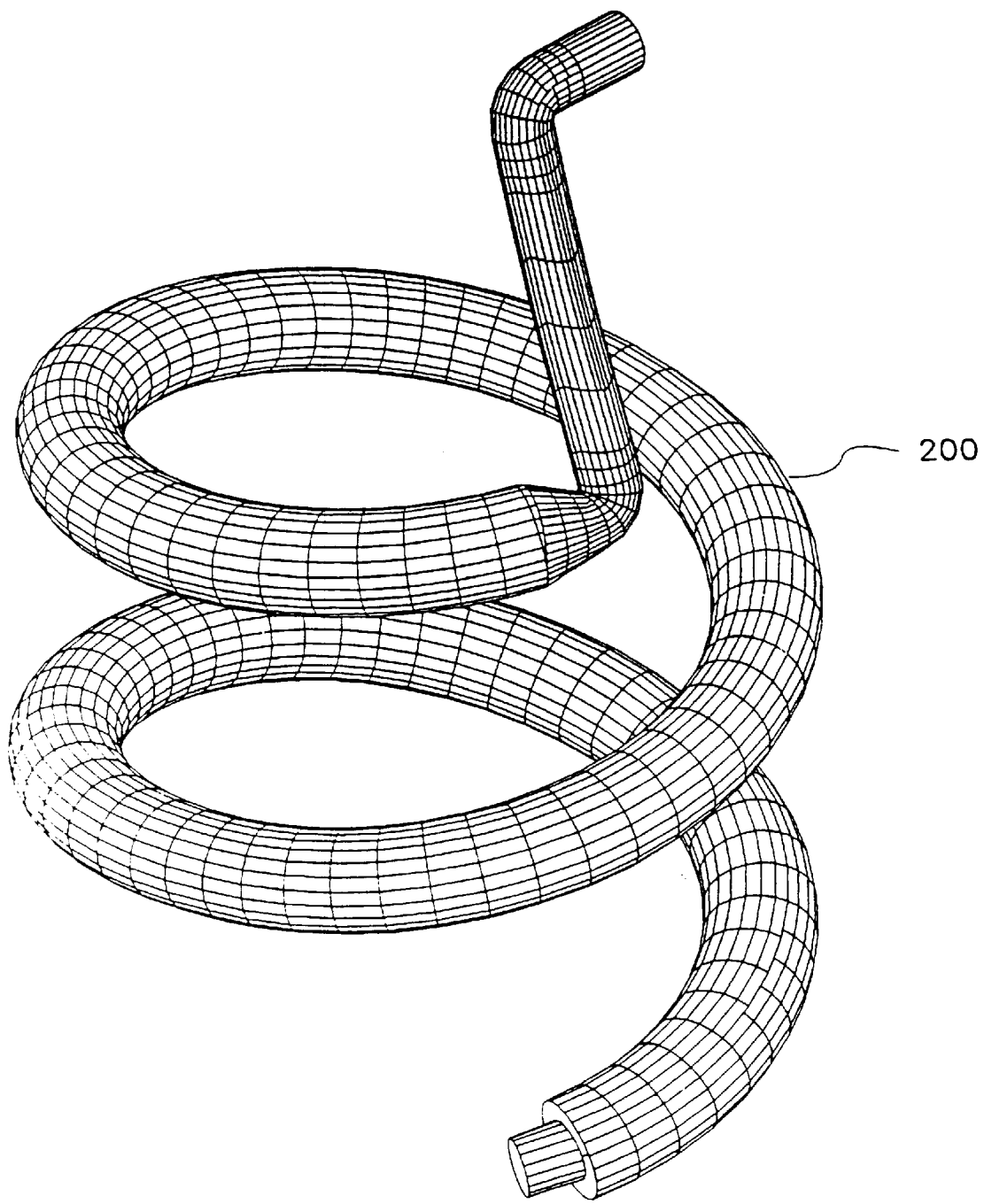
FIG. 6 shows an SMA actuator coil for the embodiment of FIG. 5.

As shown in FIGS. 5–6 another aspect of the invention utilizes a spring coil 200 as an actuator means for providing forces for moving the joint halves 102, 104 about an axis of actuation in response to thermal or electrical input. As shown in FIG. 5, spring coil actuators 200a, 200b are configured so as to be wrapped around a respective joint half 102, 104 of a joint assembly 100. The end of each actuation portion of the spring coil actuators 200a, 200b is anchored in a portion of the opposing joint half to provide a strong actuating force. Thus, the actuating end of spring coil 200a is anchored in a portion of joint half 104 and the actuating portion of spring coil 200b is anchored to joint half 102. In the embodiment shown, a fastening means 152, 154 is provided in each end of a respective joint half 102, 104.

Any convenient fastening means is possible. In the embodiment shown, the fastening means comprises a recess for receiving a respective end of each spring actuator 200a, 200b.

The joint halves 102, 104 are connected by a mechanical linkage 105 which defines an axis of actuation 106. The mechanical linkage 105 omits the capstan/pulley mechanism 112a, 112b shown in FIG. 2 and 3.

The spring coil actuator provides the advantage of producing a large deflection without the need for a pulley mechanism. The spring coil mechanism 200 as shown in FIG. 5 is capable of converting small local strains into large useful motions upon the application of electrical or thermal input.

As shown in detail in FIG. 6, the spring coil actuator 200 comprises a memory metal such as TiNi or similar material characterized by a relatively high negative or positive coefficient of thermal expansion which is electrically insulated with teflon, or the like. In a preferred embodiment, the coil comprising the actuator means 200 is sheathed with an ohmic layer an outer layer of teflon insulation to provide a low friction interface with the joint surface. The spring configuration 200 allows for a compact design, large deflection and low local strain. The spring coil actuator 200 relies on the memory effect of the SMA material such as TiNi for its performance of useful work.

Figure 7:
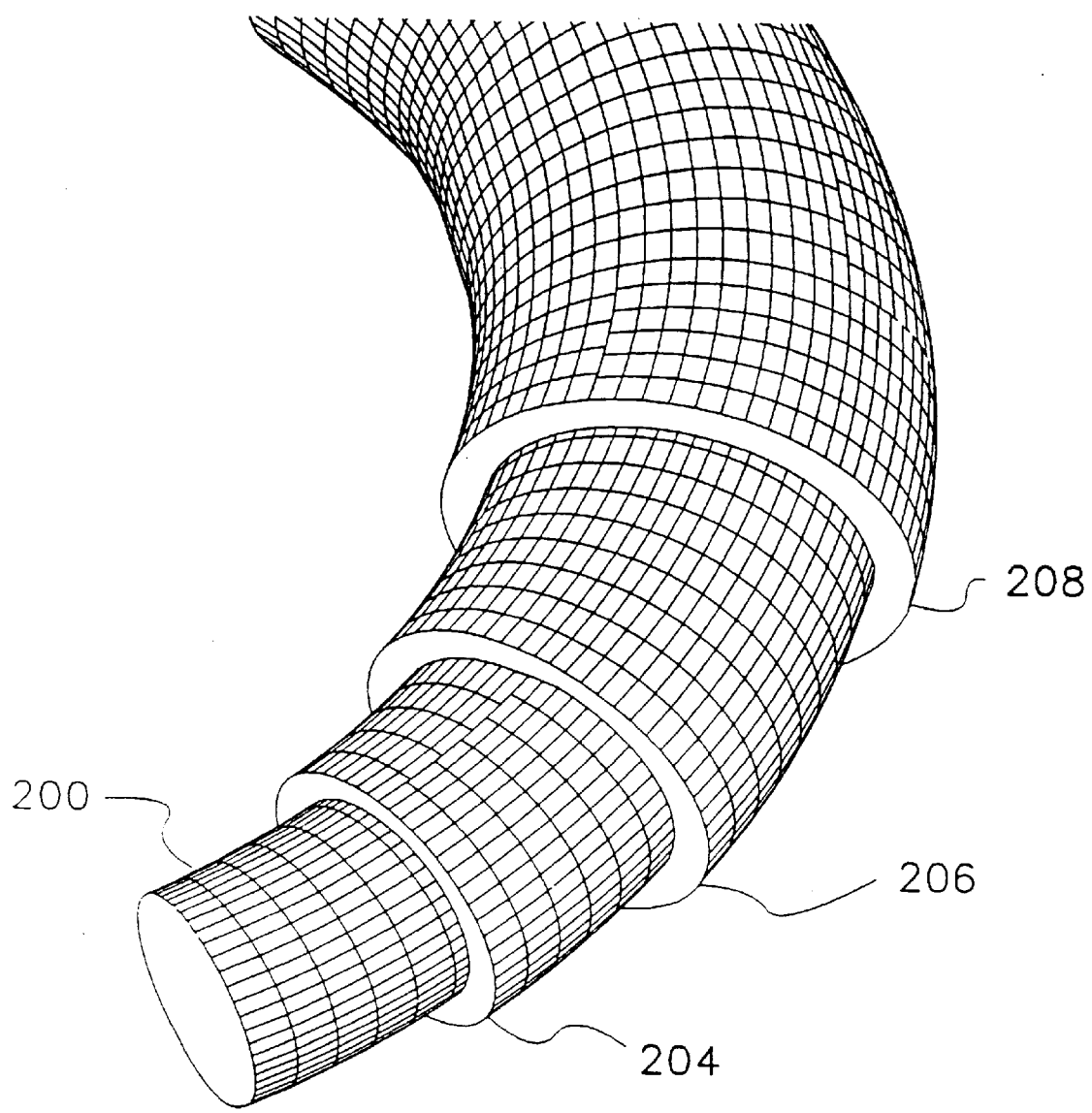
FIG. 7 shows a detail view of a restive heating scheme for an SMA actuator element according to an aspect of the present invention.

Referring to FIG. 7, the actuator 200 comprises a spring consisting of TiNi as other material exhibiting the shape memory effect. The TiNi is encased by a first layer comprising a thin film of flexible insulating polymer such as polyimide 204. This polyimide layer 204 is then seeded with a conductor such as palladium, copper, or the like. The seeded polyamide layer 204 is subsequently plated with a conductor such as a thin layer of nickel, copper, etc. 206.

It will be appreciated that the thin metallic layer 206 provides a means for indirectly resistively heating the inner coil of actuator means 200 at a greatly reduced current requirement. An outer layer 208 comprises an insulating jacket of polyamide, teflon, or the like that serves to provide electrical insulation as well as to reduce friction.

The insulating system as shown in FIG. 7 is the preferred embodiment, but one can alternatively employ an adjacent heat source for activating the TiNi which does not encapsulate the TiNi layer.

The desirable properties of the conducting layer 206 are that the material used for the conductive 206 layer be non oxidizing, and exhibit a high resistivity, such as a refractory material. This has an advantage over conventional devices by greatly reducing the current requirements for ohmic heating of a negative coefficient of expansion material such as TiNi or the like.

The thin metallic layer 206 disposed over the insulating means 204 as shown in FIG. 7 also has the advantage of enabling very small dimensioned current carrying wire to be used for carrying power to the actuator means such as TiNi coil 200. This enables the overall dimensions of the actuator joint 200, to be greatly reduced in comparison to conventional devices. This further eliminates the problem of torsional rigidity that would ordinarily be introduced by large current carrying feed wires of conventional devices, and greatly enhances the maneuverability of a device according to the present invention.

Referring again to FIGS. 2 and 3, it will be appreciated that the spatial extent of a negative coefficient of expansion material 110 or shape memory alloy actuator means 110 sheathed with an insulator 204 and ohmic heating layer 206 may be greatly reduced while maximizing the available contraction by wrapping the shape memory alloy actuator or other in the form of a coil around the circumference of each joint half 102, 104.

Referring again to FIGS. 2 and 3, the insulating material such as teflon alternatively could be disposed beneath the actuator material 110 in the form of a threaded sleeve (not shown) for maintaining spatial isolation between two adjacent coil segments 110 and for reducing friction during motion.

Actuators Characterized by Mechanical Amplification

Figure 8:
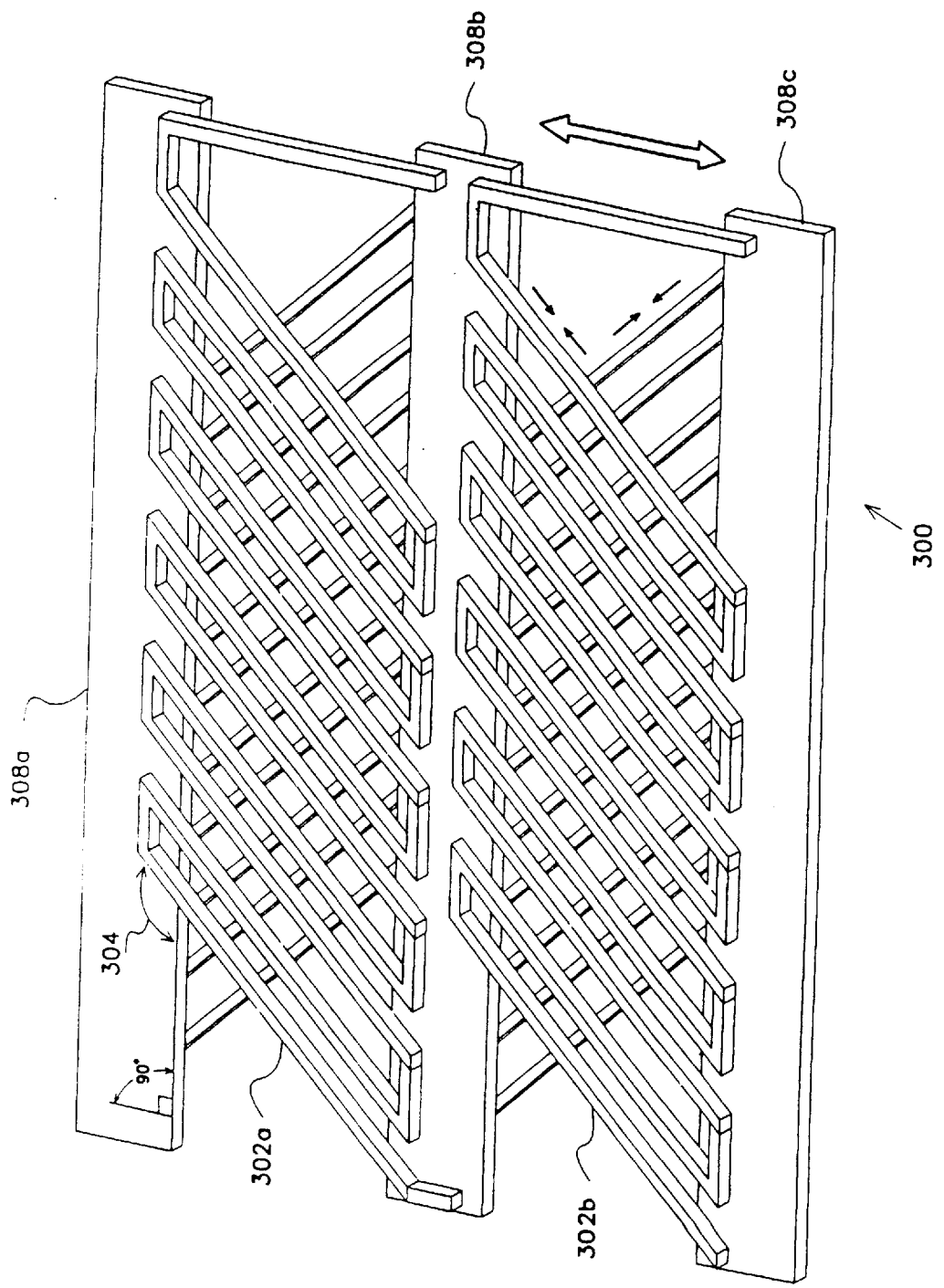
FIG. 8 perspective view of a mechanical amplification actuator scheme according to an aspect of the present invention.

In accordance with another aspect of the invention, FIG. 8 depicts an alternate configuration for the actuator means. The actuator means of FIGS. 8–10 may be substituted for the former actuator means (FIGS. 2,3,4 and 5) for providing motion between the first and second joint halves when the actuator means are activated by an applied electric current or thermal input in accordance with techniques which have been described above.

Referring to FIG. 8, an actuator means comprises a continuous path of an electrically or thermally activated material which contracts or expands upon being heated to an activation threshold. The continuous path is characterized by a skewed configuration. At least two or more sets of skewed actuator elements 302a, 302b are shown. These are linked to corresponding joint halves (not shown) by any convenient means in accordance with techniques which are well known, as shown in FIGS. 1 and 2. It is seen from FIG. 8 that the continuous paths of skewed actuator elements 302a, 302b are overlapping to provide a "scissors effect". This results in mechanical amplification when the elements 302a, 302b are supplied with an electric or thermal input which heats the material to an activation threshold.

It will be appreciated from FIG. 8 that the ratio of mechanical amplification, tradeoff between output force and deflection, can be varied to accommodate specific joint configurations. The skew angle 304 is defined with respect to horizontal anchor bars 308a, b, c as shown in FIG. 8. A 0° skew angle is parallel to the anchor bars 308a, b, c. A 90° skew angle 304 is perpendicular to the anchor bar 308c. If the skew angle 304 of the actuator material is 90°, then the achievable contraction or movement is limited to 5% of the length of the actuator material. However, the added length of actuator material when disposed in a zig-zag pattern, provides a greater range of motion than can be achieved by conventional SMA actuators.

It will be appreciated that as the skew angle 304 is decreased from 90° to 0°, this would represent an inverse cosine function and displacement increases accordingly with a corresponding drop in force. Thus, a greatly amplified range of movement can be achieved by arranging the actuator material with the skew angle as shown in FIG. 8.

Here as in the previous embodiments, the continuous skewed path 302a, 302b of shape memory alloy material, or the like, is adapted to be sheathed with a polyamide, teflon, or other insulator to reduce friction and to facilitate movement between the overlapping zig-zag paths. It will be also appreciated that the continuous skewed path of shape memory alloy material or the like maximizes the resistance over a minimum area. This has the advantage of maximizing actuator strain while reducing current requirements. This eliminates the need for large diameter current carrying wires, reduces the torsional rigidity introduced by such wires and provides a highly maneuverable device in comparison with conventional steerable catheters. In addition, the continuous skewed path maximizes the amount of recoverable displacement produced by the shape memory response.

The skewed configuration of the actuator elements 302a, 302b of FIG. 8 are anchored at oppositely disposed ends to anchor bars 308a, 308b and so forth. The anchor bars 308 are affixed to opposite joint halves of a joint as shown in FIGS. 1–3 and are adapted for transmitting the linear forces of the actuator material to each joint half as previously described.

In accordance with another aspect of the invention, the skewed path is adapted to be sheathed with both an insulator and a thin conductive outer layer as previously described. This enables the actuator element 302a, 302b to be ohmically heated by the conductive outer layer which acts as an adjacent ohmic heat source. That is, if an SMA material is used, the shape memory response is produced not by applying an electric current to the shape memory material 302a, 302b directly, but rather the current is applied to the outer conductive layer. Thus, the outer conductive layer then ohmically heats the shape memory alloy 302a, 302b to the activation threshold. This provides the advantage of a greatly reduced current demand and also enables more precise control of the activation threshold.

High Strain Serpentine SMA Actuator

Figure 9:
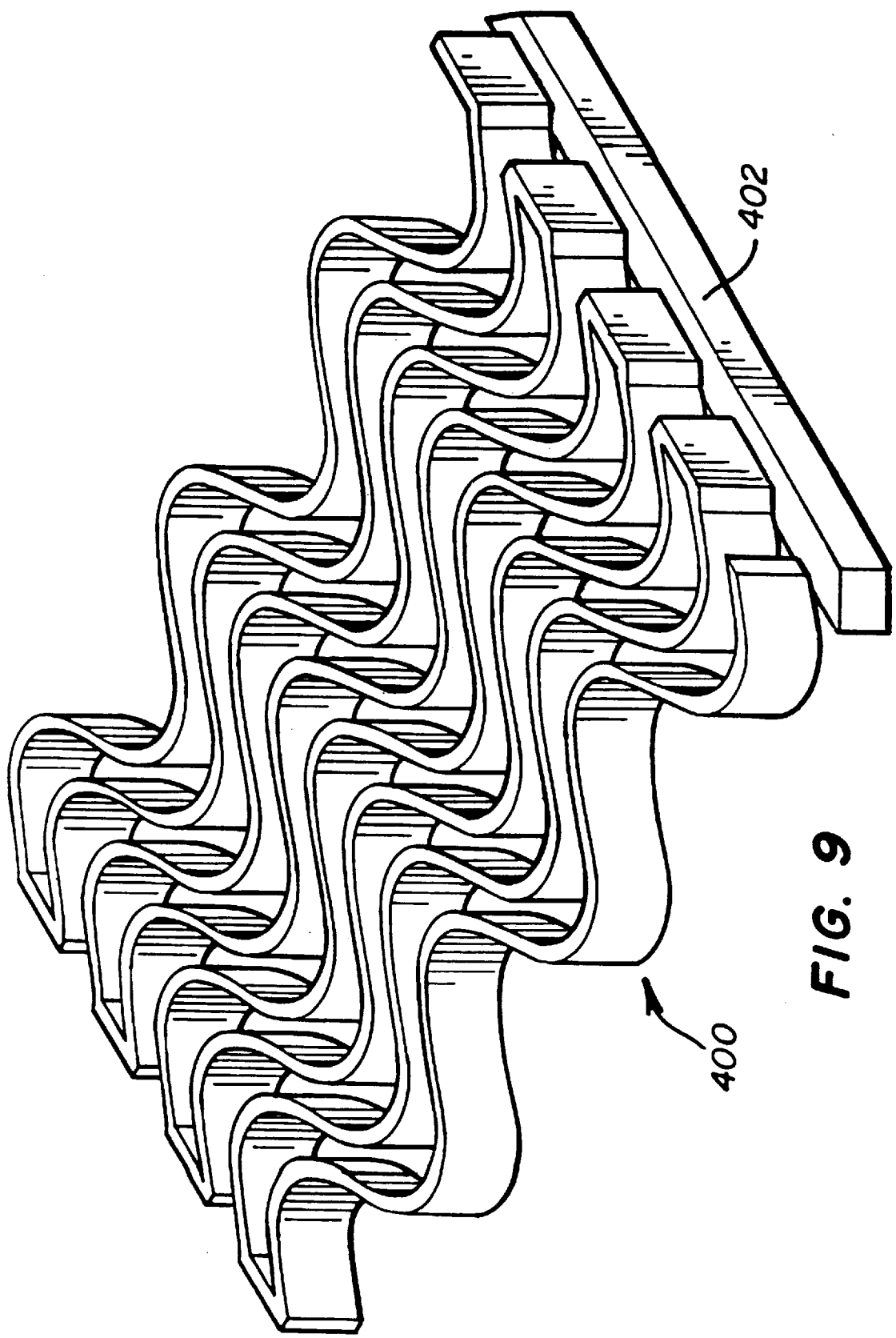
FIG. 9 shows a serpentine spring configuration for an actuator according to an aspect of the present invention.

As shown in FIG. 9, a serpentine SMA actuator 400 comprises a compact, continuous path of SMA material that folds back on itself in such a way that it produces large linear motions while providing a high resistance, low heating current path.

The serpentine structure is manufactured using standard VLSI micromachining techniques for very small actuators. Alternatively, the serpentine structure may be stamped from sheets of shape memory alloy for larger devices. Anchor bars 402 are affixed at either end of the SMA element and provide means for transmitting linear forces to the environment; only one anchor bar is shown for clarity. As in a conventional helical spring, the overall "strain"or lengthening of the serpentine spring is much greater than the local strain of the spring material at any point. For example, a local strain of 5% might translate into a 100% change in overall length of the actuator.

By utilizing a long continuous path of material 400, the ohmic heating resistance of the spring can be made very high. Adjacent portions of the spring must be electrically isolated from one another. One approach might be to cast the entire device in a very compliant elastomer.

Factors such as thickness and height of the serpentine spring will affect strain limits and hence, the elongation potential. A very slender aspect ratio will limit the device to a contraction mode of operation due to buckling constraints.

This provides a compact, planar configuration for mechanically transforming the high force, low strain output of SMAs to provide a more useful high strain, low force output. A compact high strain, high force actuator can be made by combining a number of serpentine actuators in parallel.

A serpentine, planar spring actuator according to this aspect of the invention provides significant advantages over conventional SMA actuators. A serpentine actuator comprising a planar spring may be manufactured using VLSI techniques.

A planar spring actuator amplifies linear motions while requiring less than a 5% deflection at the material level. Thus maximizing useful movement when down-sized. An actuator configured as a long, continuous path provides a high resistance, low current path for smaller feed wires. This thereby enables an endoscope, bronchoscope, or the like incorporating SMA actuator joints according to this aspect of the invention to be considerably downsized. Further, the configuration according to this aspect of the invention is inherently flexible and overcomes the problem of torsional rigidity in conventional endoscopes.

High Strain Wave SMA Activator

Figure 10:
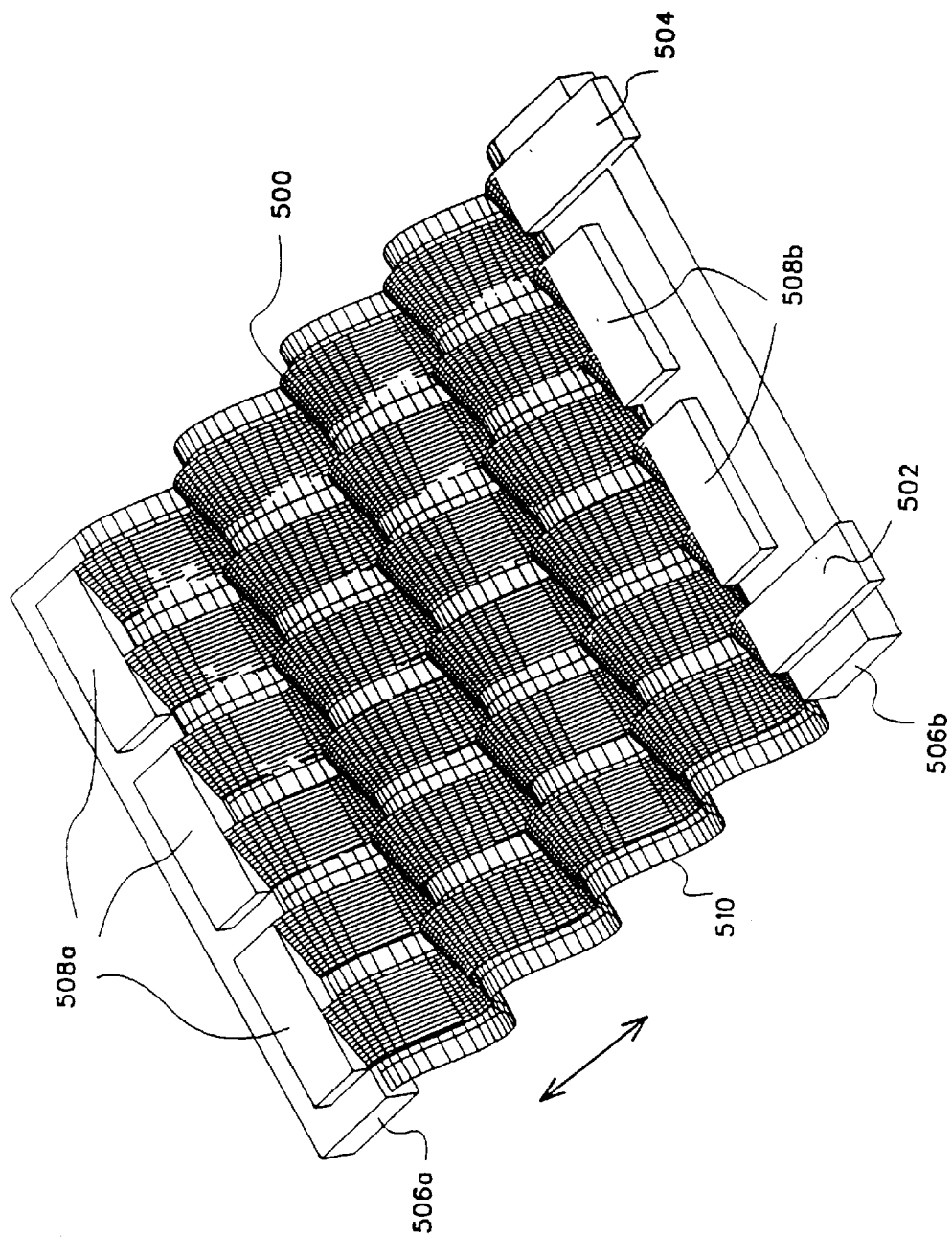
FIG. 10 shows a "wave" configuration for an actuator according to an aspect of the invention.

FIG. 10 shows another embodiment of SMA actuator which is adapted to move the joint halves of a joint assembly as explained with reference to FIGS. 1–3.

The wave SMA actuator is similar in function to the serpentine device of FIG. 9. It too can produce a very large deflection while maintaining low strain at the local level. It can also be formed with conventional VLSI methods or can be stamped from a sheet of SMA. This activator configuration is characterized by a continuous, folded wavelike configuration of SMA material 500 to provide a high resistance path that reduces current demand and permits the use of smaller gauge feed wires. A power lead 502 is provided for connecting to a positive supply or other source of electric current. A ground lead 504 provides a return path. Anchor bars 506a, 506b are provided for transmitting the linear forces produced by the actuator 500 to respective joint halves. The strips of SMA material are connected through conductive connectors 508a, 508b disposed on the anchor bars. A flexible substrate 510 comprising a polyimide or kevlar based material acts as a base for supporting the SMA actuators 500.

The essential difference between the serpentine SMA actuator and wave SMA actuator lies in the direction of the periodic spring structure. Whereas the serpentine spring lies wholly within a plane and meanders laterally, the wave spring exhibits a vertical periodicity. It will be appreciated that both the serpentine and wave actuators provide the advantage of maximized movement which overcomes the 5% linear contraction limitation of conventional SMA actuators.

Concatenated Joint Assembly

Figure 11:
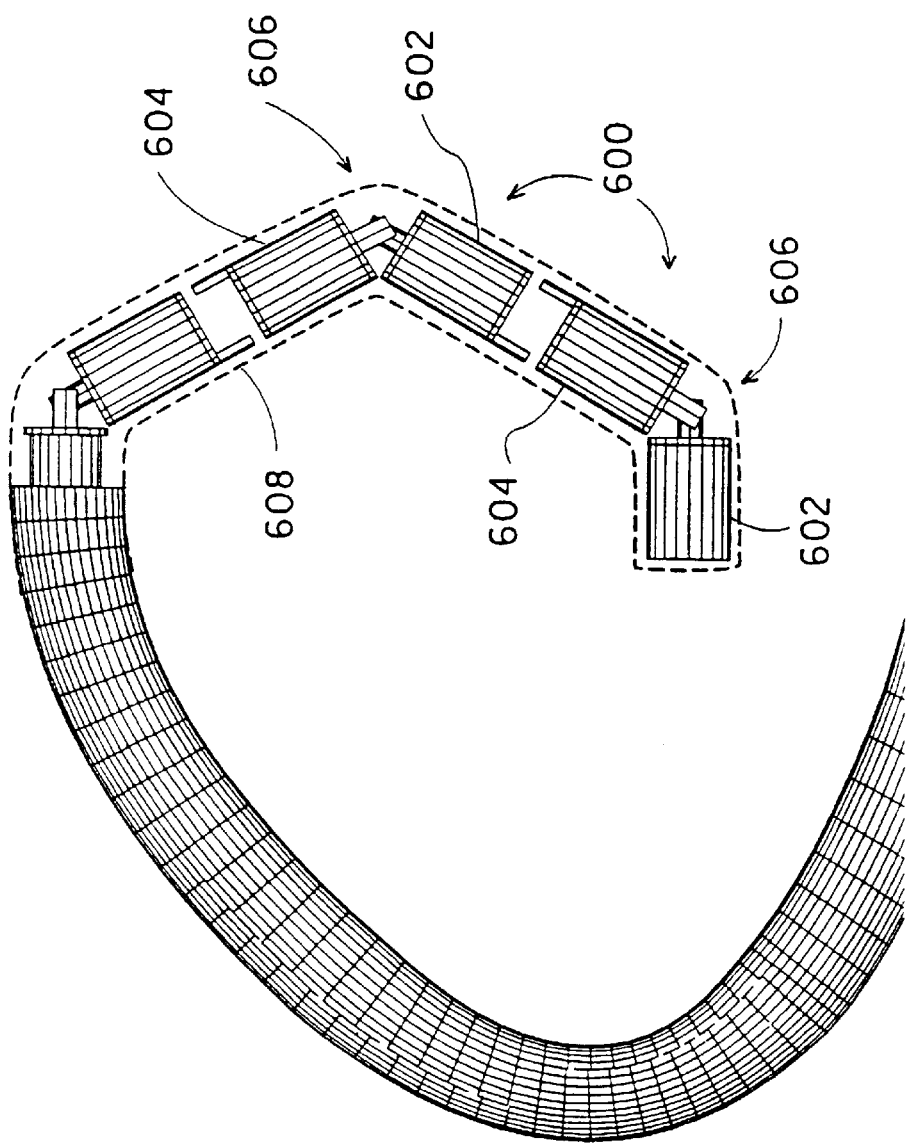
FIG. 11 is a perspective view of another aspect of the present invention showing the concatenation of a plurality of SMA actuator joints.

Referring to FIG. 11, in order to provide a full three degrees of freedom in three dimensional space, a plurality of single axis joints 600 must be concatenated in such a way that their axes of actuation do not coincide. Each single axis joint 600 comprises two corresponding joint halves 602, 604, operatively joined at an axis of actuation 606. A minimum configuration requires that each joint be rotated 90 degrees with respect to the previous joint. However, any relative rotation is possible. This would give full access to any point in three dimensional space about the multi-jointed manipulator.

With an appropriate bend angle (at the actuation axis 606) defined by an external controller and communicated to each predetermined joint through a flexible microcable, any desired configuration can be generated in a precise fashion in accordance with techniques which are well known. The number of joints 600 that can be concatenated is primarily limited by the number of corresponding actuators which can be physically activated by the current carrying microcable (see FIG. 12) which connects the joints.

An external, flexible sheath 608 comprising a surgical elastomer material is provided over the concatenated joints. The elastomer material is adapted to provide ease of movement and maneuverability for medical or surgical applications.

Microcable

Figure 12:
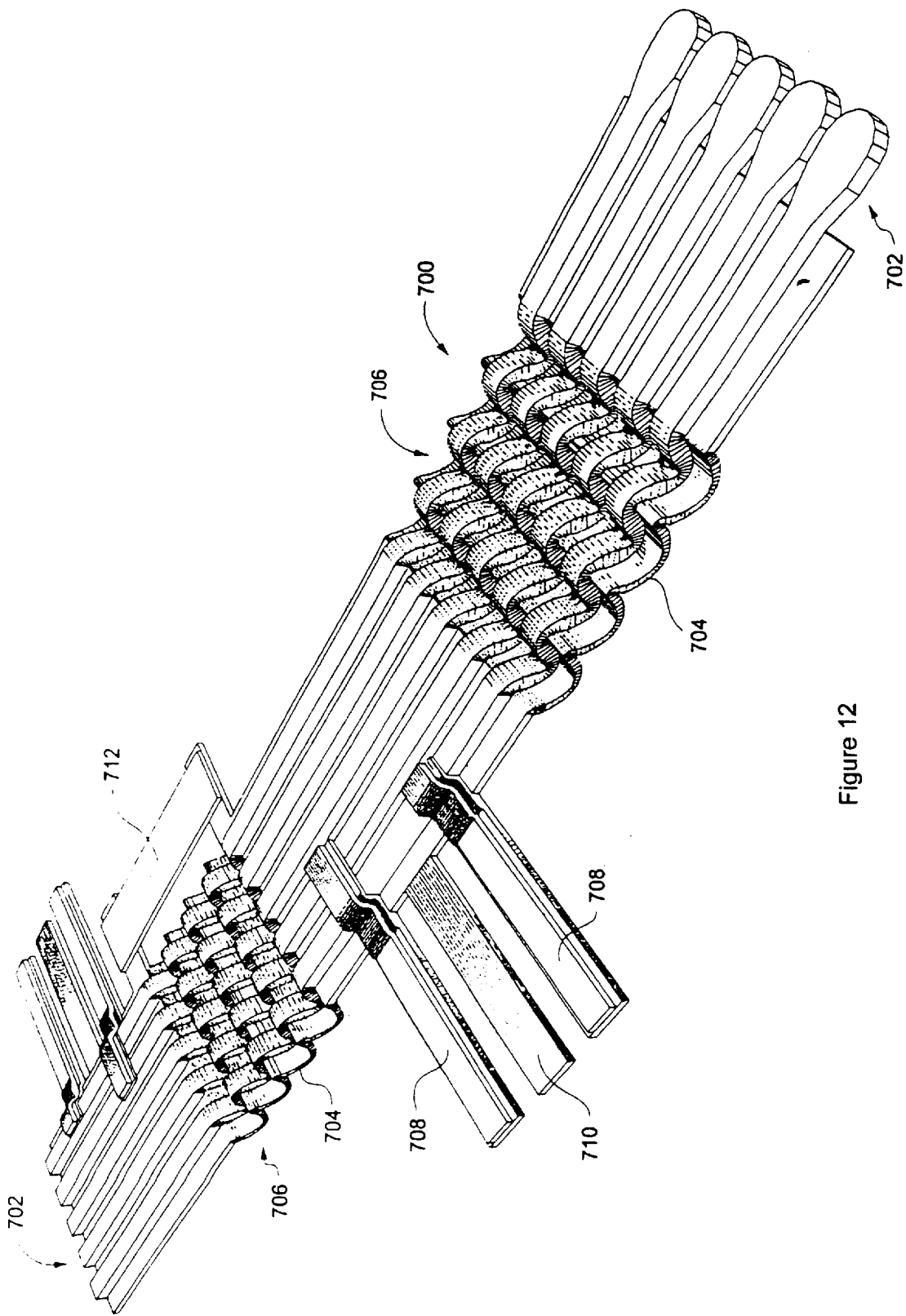
FIG. 12 shows a microcable in accordance with another aspect of the present invention for coordinating the activation of a plurality of joints.

FIG. 12 depicts a microcable 700 for concatenating a plurality of joints. The microcable 700 consists of a plurality of thin conductive leads 702 plated on a flexible sheet of polyimide 704 or the like. The conductive leads are power leads and are connected with a power source for providing an electric current of a predetermined activation threshold to the joint actuators (not shown for clarity). Gold is a preferred material for conductive leads 702, since it is malleable and can be fabricated in wire form at extremely small dimensions, as small as two microns.

It will be appreciated that the joint actuators and joint assemblies of the present invention are adapted to be micromachined to extremely small dimensions, e.g., as small as 50 microns. The lower size limit is determined by the desired amounts of torque to be transmitted and the surgical or other application to be addressed. The microcable 700 provides a means for controllably concatenating a plurality of joint assemblies to provide an integrated plurality of joint assembles which can be controlled as a whole to substantially increase the range of motion and maneuverability over a conventional catheter, endoscope or the like. a set forth above, a conventional endoscope is limited to at most two joints.

In a first embodiment, as shown in FIG. 9, the microcable comprises a plurality of corrugations 706 disposed in the power leads 702. The corrugations provide a means for enabling the microcable to flex as the plurality of concatenated joints are activated. As will be appreciated from FIG. 9, each joint requires only a power lead 708 and a ground lead 710 which extend from a respective conductive lead 702 and common ground plane (not shown). The ground plane is incorporated as an interlayer sandwiched between two layers of polyamide which comprise the polyamide substrate 704. The ground plane is thus incorporated in the microcable in accordance with techniques which are well know.

A conventional strain gauge 712 may be disposed across each corrugated or pleated region in the microcable. The bend angle of the joint imposes a linear strain in the pleated region 706 of the cable 700. From this, the strain gauge 712 provides a means for inferring angular joint displacement.

It will be appreciated that the microcable provides a means for distributing electrical power to each actuator element on each joint. The microcable comprises a flexible, multi-conductor cable. A plurality of conductive current carrying pathways are provided by conductive leads 702 which are deposited on the flexible substrate in accordance with VLSI techniques which are well known. The preferred material for conductive leads 702 is pure gold or any other flexible conductor resistant to work hardening and characterized by low resistance. The conductors 702 are physically separated from one another and are adapted to be completely encased, encapsulated or potted in a medium such as a silicon elastomer elastic in accordance with well known techniques. An overall conductive layer could be deposited over the microcable for EMF shielding.

Pleated sections 706 of microcable 700 are incorporated along the entire length of the cable at intervals corresponding to the distance between successive joint axes. The individual electrical signals for activating the joint halves are communicated along leads extending from the straight cable sections between the corrugations.

In practice, the microcable is disposed along the length of a number concatenated joints. The pleated or corrugated sections are positioned at the joint gaps. The pleated sections can accommodate bending in any direction as well as withstand torsional twisting and extension. As in a multi-layer PC board, an intermediate conducting layer extending the width of the cable preferably comprises a ground plane. All returning activation current then would flow through the ground plane.

Microcable Comprising Active Elements

Figure 13:
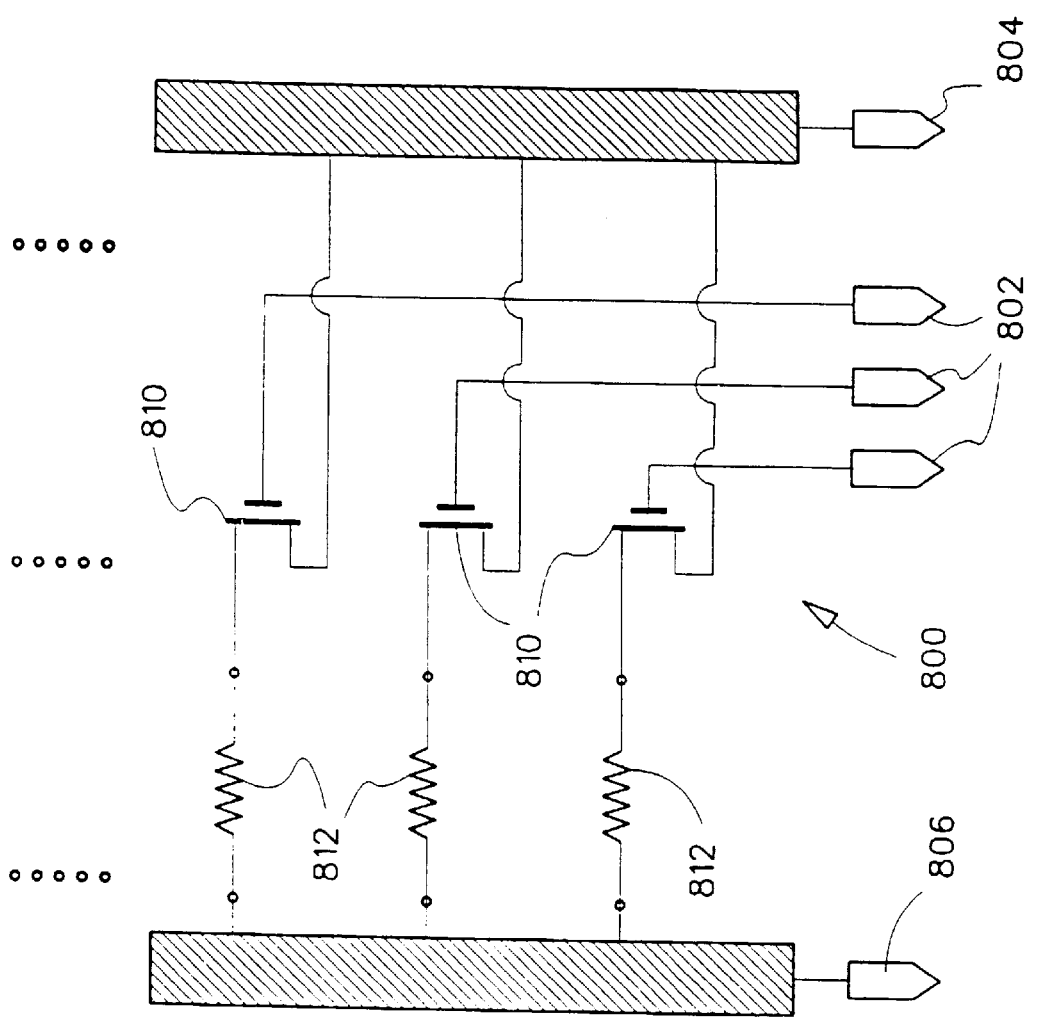
FIG. 13 is a schematic drawing of a microcable with active electronic elements according to an aspect of the present invention.

In accordance with another aspect of the invention, a microcable 800 as shown in FIG. 13 comprises a plurality of data signal leads 802, a positive supply lead, $V_{cc}$ (shown at 804), a ground lead 806, and a plurality of analog switch means 810 for selectively coupling thermal or electrical activation energy into joint actuators 812 in response to a signal applied over data signal leads 802. In this embodiment it will be appreciated that a plurality of concatenated joints are each provided with a corresponding actuator, shown as a load 812. All of the actuators 812, and consequently all of the concatenated joints, are electrically connected by the microcable 800.

The data signal leads 802 and the positive supply or power lead 804 are deposited by conventional VLSI techniques, or otherwise provided on a flexible substrate such as a polyimide based material (not shown for clarity). The ground lead 806 is preferably configured as a common ground plane provided in and insulated by the substrate to prevent crosstalk, in accordance with well known techniques.

It will also be appreciated that the data signal leads 802 do not carry current, but merely an activation signal. Thus, the data signal leads 802 can be deposited with extremely small dimensions on the surface of the substrate. Alternatively, the data signal leads can be incorporated in sequential layers within the substrate. Since each joint has a dedicated data signal lead 802, this aspect of the invention has the advantage of enabling a large number of data signal leads to be provided in the microcable. This increases the number of joints which can be electrically activated for desired movement.

The microcable is adapted to coordinate the movement of a large number of joints. This is accomplished by incorporating in the microcable a plurality of corresponding active elements, preferably FET analog switches 810. Any switch, such as a solid state or micromachined switch may be employed. What is required is that the switch comprise a means for passing thermal or electrical activation energy to a load, actuators 812, in response to a data signal applied to a data signal lead or gate 814.

Alternatively, other equivalent voltage controlled switches or means for passing a signal through to a load may be employed. It will be appreciated that each joint in the concatenated joint assembly has its own corresponding FET switch and a dedicated data signal lead 802. However, the data signal leads 802 carry only a minimum voltage for selectively enabling a corresponding FET switch 810. Thus, the data signal leads 802 can be considerably downsized. Consequently, the microcable 800 advantageously can be significantly reduced in size in accordance with this aspect of the invention.

As shown in FIG. 13, each FET switch 810 has a gate 814 connected to the data signal lead 802. The common $V_{cc}$ line 804 for all joints is connected to a power input lead or source of each FET switch. The output lead or drain of each FET switch 810 is connected to one end of a corresponding joint actuator 812. The other end of the joint actuator 812 connects to the common ground 806.

In operation, data signals are modulated to the gates 814 of selected FET switches 810 on the data signal leads 802 in accordance with well known pulse width modulation schemes.

A data signal of a predetermined threshold appearing on the gate 814 of FET switch 810 activates the switch and sends the activation current on line 804 to the joint actuator 812 associated with the corresponding activated FET switch 810. A conventional pulse width modulation scheme can be used to activate the joint to a predetermined bend angle and to maintain the angle for a predetermined period of time. The return current path is provided through 806, which is preferably a ground plane incorporated in the microcable 800 as previously explained.

The microcable 800 incorporating a plurality of active elements, one corresponding to each joint, has the advantage of enabling a greatly increased number of joints to be controllably activated in a coordinated fashion because the microcable 800 comprises only a single power lead 804. This advantageously reduces the size and complexity of the microcable. It will be appreciated that a microcable in accordance with this aspect of the invention is capable of being downsized to the extent that it can power and coordinate the activation of a plurality of micromachined joints, without causing a loss of maneuverability.

While the invention has been described in connection with what is presently considered to be the most practical and preferred embodiments, it is to be understood that the invention is not limited to the disclosed embodiment but, on the contrary is intended to cover various modifications and equivalent arrangements included within the spirit and scope of the appended claims.

For example, it will be appreciated by one skilled in the art that an equivalent actuator for those according to the present invention would be one which provides a strong contractive or expansive force upon the application of a electrical or thermal input. For example a bimorphous material piezo constrictive material, magneto-restrictive material or the like could be substituted for the SMA actuators described herein. Also, equivalent structures for providing mechanical amplification, can be employed. For example, a folded continuous path of SMA material could be combined with gears to provide mechanical amplification.

Therefore, persons of ordinary skill in this field are to understand that all such equivalent structures are to be included within the scope of the following claims.

What is claimed is:

1. A method for moving a joint assembly with a material characterized by a negative coefficient of expansion upon being heated to an activation threshold, comprising the steps of:

providing a first joint half;

connecting a second joint half with said first joint half for enabling said joint formed by both halves to be moved with at least one degree of freedom;

providing a strip of said negative coefficient of expansion material for transmitting actuating forces to each joint half;

reducing the spatial extent of said negative coefficient of expansion material by wrapping one end around the circumference of each joint half;

providing electrical connections for resistively heating said strip of negative coefficient of expansion material to an activation threshold.

2. A joint assembly comprising:

a first joint half;

a second joint half movably connected to said first joint half at an axis of actuation;

actuator means disposed about the circumference of at least one joint half for providing a pulling force upon being heated to an activation threshold;

mechanical linkage means for transforming said pulling force to a torque about said axis of actuation.

3. An apparatus according to claim 2 wherein said actuator means comprises a folded continuous path of a material characterized by a negative coefficient of expansion, such that any two adjacent segments of said folded path are electrically isolated, and the length of said material characterized by a negative coefficient of expansion is maximized for a given area to thereby maximize electrical resistance and reduce current demands for heating said actuator means.

4. An apparatus according to claim 2 wherein said mechanical linkage means comprises a means for rotating said axis of actuation of a first joint half about the longitudinal axis of said joint assembly with respect to the other joint half.

5. An apparatus according to claim 2 wherein said joint assembly comprises a hollow central bore for receiving optical imaging devices therein.

6. An apparatus according to claim 2 wherein said joint assembly comprises a hollow central bore for receiving surgical devices.

7. A joint assembly comprising:
a first joint half;
a second joint half movably connected to said first joint half at an axis of actuation;
actuator means comprising a continuous sheet of two-way shape memory alloy material wrapped around the circumference of at least one of said joint halves for providing rotation of said joint halves in either direction about a longitudinal axis when said shape memory alloy material is heated to an activation temperature.

8. A joint assembly comprising:
a first joint half;
a second joint half substantially aligned with the first joint half along a longitudinal axis and connected to said first joint half at an axis of actuation;
actuator means comprising a substantially continuous sheet of two-way shaped memory alloy material wrapped around the circumference of at least one of said joint halves for providing movement of said at least one joint half about said axis of actuation and perpendicular to said longitudinal axis upon being heated to an activation threshold.

9. A joint assembly comprising:
a first joint half;
a second joint half connected to said first joint half at an axis of actuation for providing one or more degrees of freedom of angular motion of said joint assembly;
actuator means for providing motion between said first and second joint halves, due to shape memory response when said actuator means are heated by an applied electric current to an activation threshold, wherein said actuator means comprise a means for mechanically amplifying the motion produced by said shape memory response.

10. An apparatus according to claim 9 wherein said means for amplifying the motion produced by said shape memory response comprise one or more elements comprising a material characterized by a negative coefficient of expansion wherein said one or more elements are configured in a continuous zig-zag path for providing an amplified pulling force upon being heated to said activation threshold.

11. An apparatus according to claim 9 wherein said means for amplifying motion comprises a continuous, overlapping zig-zag path of two way shape memory alloy material.

12. An apparatus according to claim 9 wherein said means for amplifying motion comprises at least two or more antagonistically disposed elements comprising a continuous, zig-zag path of one-way shape memory alloy material which path amplifies the movement produced when said shape memory alloy material is heated to an activation threshold.

13. An apparatus according to any one of claims 9–12 wherein said actuator means is ohmically heated to an activation threshold by an adjacent ohmic heat source.

14. A joint assembly comprising:
a first joint half;
a second joint half connected to said first joint half at for providing one or more degrees of freedom of angular motion;
actuator means for providing actuating forces between said first and second joint halves upon being electrically activated, wherein said actuator means comprise a continuous conductive path of folded material for minimizing current demand upon application of an electric current, said continuous conductive path of material providing a strong contracting force upon being resistively heated to an activation threshold.

15. An apparatus according to claim 14 wherein said actuator means comprises a shape memory alloy material exhibiting one-way shape memory.

16. An apparatus according to claim 14 wherein said actuator means comprises means for mechanically amplifying small motions through a skewed configuration of adjacent layers of said continuous conductive paths of material.

17. An apparatus according to claim 14 wherein said folded continuous conductive path of material is adapted to be manufactured using VLSI techniques when extreme miniaturization is required.

18. An apparatus according to claim 14 wherein said actuator means further comprise a flexible isolation means provided for electrically isolating adjacent layers of said folded conductive path of material.

19. A joint assembly comprising:
a first joint half;
a second joint half connected to said first joint half for providing one or more degrees of freedom of angular motion of said joint assembly;
actuator means for providing actuating forces between said first and second joint halves upon being electrically activated wherein said actuator means comprises a continuous band of material affixed to said first and second joint halves for providing actuating forces to said joint assembly, said continuous band of material comprising a material characterized by providing a pulling or pushing force upon being electrically activated.

20. An apparatus according to claim 19 wherein said continuous band of material comprises a plurality of corrugations for providing mechanical amplification of motion upon being electrically activated.

21. An apparatus according to claim 19 wherein said actuator means comprises a material characterized by a high thermal coefficient of expansion.

22. An apparatus according to claim 21 wherein said actuator means is heated via an adjacent heat source.

23. An apparatus according to claim 21 wherein said actuator means comprises a shape memory alloy material characterized by two-way or one-way shape memory.

24. An apparatus according to claim 21 wherein said actuator means comprises an electroconstrictive material.

25. A joint assembly comprising:
a first joint half;
a second joint half connected to said first joint half at an axis of actuation for providing one or more degrees of freedom of angular motion;
actuator means for providing actuating forces between said first and second joint halves upon being electrically activated, wherein said actuator means comprises an electrically activated spring comprising shape memory alloy material disposed about the circumference of at least one of said joint halves for maximizing the available contraction of said shape memory alloy material.

26. An apparatus according to claim 25 wherein said actuator means comprises a spring comprising shape memory alloy material for providing a large displacement upon being electrically activated.

27. An apparatus according to claim 25 wherein said spring is characterized by a material having no more than 5% strain within a given volume thereof.

* * * * *

UNITED STATES PATENT AND TRADEMARK OFFICE

CERTIFICATE OF CORRECTION

PATENT NO. : 5,996,346

DATED : December 7, 1999

INVENTOR(S) : Ronald S. MAYNARD

It is certified that error appears in the above-identified patent and that said Letters Patent is hereby corrected as shown below:

In column 15, line 5, "means" should be --means,--.

Signed and Sealed this

Twelfth Day of September, 2000

Attest:

Q. TODD DICKINSON

*Attesting Officer*       *Director of Patents and Trademarks*